United States Patent
Voeller et al.

(10) Patent No.: US 10,293,087 B2
(45) Date of Patent: May 21, 2019

(54) VACUUM ASSISTED DRAIN CONNECTOR AND ASSEMBLY

(71) Applicants: Guy R. Voeller, Germantown, TN (US); David L. Webb, Jr., Memphis, TN (US); Nathaniel Stoikes, Cordova, TN (US)

(72) Inventors: Guy R. Voeller, Germantown, TN (US); David L. Webb, Jr., Memphis, TN (US); Nathaniel Stoikes, Cordova, TN (US)

(73) Assignee: Vacuus, LLC, Germantown, TN (US)

( * ) Notice: Subject to any disclaimer, the term of this patent is extended or adjusted under 35 U.S.C. 154(b) by 382 days.

(21) Appl. No.: 15/206,865

(22) Filed: Jul. 11, 2016

(65) Prior Publication Data

US 2017/0157306 A1    Jun. 8, 2017

Related U.S. Application Data

(60) Provisional application No. 62/262,522, filed on Dec. 3, 2015.

(51) Int. Cl.
*A61M 39/10* (2006.01)
*A61M 1/00* (2006.01)

(52) U.S. Cl.
CPC ...... *A61M 1/0086* (2014.02); *A61M 39/1011* (2013.01); *A61M 2039/1033* (2013.01)

(58) Field of Classification Search
CPC .. A61M 2039/1033; A61M 2039/1027; A61M 39/1011; A61M 1/0086
See application file for complete search history.

(56) References Cited

U.S. PATENT DOCUMENTS

| | | | |
|---|---|---|---|
| 3,876,234 A | 4/1975 | Harms | |
| D303,013 S | 8/1989 | Konopka | |
| 5,009,252 A * | 4/1991 | Faughn | F16L 37/113 137/614.04 |
| D454,637 S | 3/2002 | Nestenborg | |
| D483,869 S | 12/2003 | Tran et al. | |
| 7,699,831 B2 * | 4/2010 | Bengtson | A61M 1/0088 604/313 |
| D639,398 S | 6/2011 | Wilhelm | |
| 2003/0204127 A1 * | 10/2003 | Rawles | A61M 1/1698 600/16 |
| 2005/0001425 A1 * | 1/2005 | deCler | F16L 37/0841 285/305 |
| 2005/0101939 A1 * | 5/2005 | Mitchell | A61M 39/10 604/533 |

(Continued)

*Primary Examiner* — Susan S Su

(74) *Attorney, Agent, or Firm* — Capitol City TechLaw

(57) ABSTRACT

A vacuum assisted drain connector ("VAD connector") may be used to connect a surgical drain to a portable electronic vacuum device. The VAD connector may have an elongate body with a nipple connector at one end and a twist lock feature at the other end. A through passage may extend between an inlet opening provided in the nipple connector and an outlet opening provided in the twist lock feature. The nipple connector may be connected to the proximal end of a surgical drain, which is to be implanted in a patient's body. The twist lock feature may be connected to a cooperating twist lock feature provided on a native vacuum tube of portable electronic vacuum pump.

9 Claims, 3 Drawing Sheets

(56) References Cited

U.S. PATENT DOCUMENTS

| | | | |
|---|---|---|---|
| 2005/0225082 A1* | 10/2005 | Dalle | A61M 39/1011 285/330 |
| 2007/0025811 A1* | 2/2007 | Wilhelm | F16L 37/34 403/300 |
| 2007/0282310 A1* | 12/2007 | Bengtson | A61M 1/0088 604/543 |
| 2008/0007051 A1* | 1/2008 | Jensen | F16L 37/00 285/305 |
| 2008/0129042 A1* | 6/2008 | Weigel | A61M 39/1011 285/92 |
| 2009/0163893 A1 | 6/2009 | Opie et al. | |
| 2009/0188575 A1* | 7/2009 | Williams | F16L 37/0985 137/798 |
| 2009/0281526 A1* | 11/2009 | Kenny | A61M 1/0088 604/543 |
| 2010/0056975 A1* | 3/2010 | Dale | A61M 1/16 604/6.16 |
| 2010/0286596 A1* | 11/2010 | Hofmann | A61M 1/008 604/35 |
| 2012/0209057 A1* | 8/2012 | Siess | A61M 39/1011 600/16 |
| 2013/0310809 A1* | 11/2013 | Armstrong | A61M 1/0088 604/543 |
| 2013/0317483 A1* | 11/2013 | Reichart | A61M 27/00 604/541 |
| 2014/0371725 A1* | 12/2014 | Karimov | A61M 27/00 604/541 |
| 2015/0238747 A1* | 8/2015 | Russo | A61M 39/1011 604/533 |
| 2016/0131292 A1* | 5/2016 | Decker | F16L 37/086 285/317 |

* cited by examiner

VACUUM ASSISTED DRAIN CONNECTOR AND ASSEMBLY

This application claims priority under 35 USC 119(e) to U.S. Provisional Application No. 62/262,522 filed on Dec. 3, 2015, the entire content of which is incorporated herein by reference.

BACKGROUND

1. Field

Non-limiting embodiments relate in general to devices that are used to remove fluids from wounds, and more particularly, to a connector that provides a fluid tight connection between a surgical drain and a portable electronic vacuum device.

2. Discussion of Related Art

Numerous and varied drain systems are employed to remove pus, blood, or other fluids from wound sites. Closed-drain systems involve the use of flexible tubing that drain into a reservoir. And some closed-drain systems are "active" meaning that they are maintained under suction. Fluid collection sites may include surface wounds (or open wounds) and internal wounds (or closed wounds). According to conventional wisdom, the particular closed-drain system and the active suction source employed depend on the wound site involved.

Closed-Drain Systems for Actively Draining Closed Wound Sites:

A surgical drain (or bulb drain) may be employed to actively remove fluid from a closed wound site. The surgical drain is in the form of a flexible tube. The tube has a distal end that is placed into the patient's body for drainage of fluids from the wound site. The distal end may have surface features (e.g., openings, perforations, channels, etc.) for passage of fluid into the tube. The distal end typically has a flattened, oval, or circular shape. The tube also has a proximal end with a circular shape for connection to a nipple connector of a flexible bulb. The proximal end of the tube is stretched over the nipple connector of the bulb to provide a fluid tight connection between them.

The bulb serves as an active suction source and a collection reservoir. With a port in the bulb opened, the bulb is compressed to remove air. The port is then closed and the bulb is released to create negative pressure within the tube as the bulb returns to its normal shape.

Closed-Drain Systems for Actively Draining Open Wound Sites:

A sealed wound dressing connected to a vacuum pump may be employed to actively remove fluid from an open wound site. Here, a dressing (e.g., foam or gauze) is fitted to the contours of the wound, and then sealed with a film. One end of a flexible drainage tube is connected to the dressing through an opening of the transparent film. The other end of the drainage tube is provided with a twist lock feature (e.g., the male part or plug) that cooperates with a twist lock feature (e.g., the female part or receptacle) of a vacuum tube to provide a fluid tight connection between them. The vacuum tube extends to a reservoir of a portable electronic vacuum pump. The vacuum tube is "native" to the portable electronic vacuum pump meaning that it is permanently connected to the vacuum pump. The twist lock features provide a mechanism by which the drainage tube can be disconnected from the vacuum tube (and thus the vacuum pump) to allow for a dressing change.

The vacuum pump power is turned on to create negative pressure within the vacuum tube and the drainage tube.

Although conventional closed-drains systems are generally thought to provide acceptable performance, they are not without shortcomings. For example, the equipment and component parts of available closed-drain systems are designed for specific applications (i.e., dedicated to treat a particular type of wound). The surgical drains available for closed wound sites and the portable electronic vacuum pumps available for open wound sites cannot be used together in one drain system due to structural incompatibility.

SUMMARY

According to a non-limiting embodiment, an assembly may include a connector having a nipple connector with an inlet opening, and a first twist lock feature with an outlet opening. A through passage may extend between the inlet and the outlet openings. The assembly may also include a surgical drain that may have a distal end to be implanted in a patient's body, and a proximal end stretched over the nipple connector to provide a fluid tight connection between the surgical drain and the connector. The assembly may also include a portable electronic vacuum pump that has a collection reservoir and a vacuum tube that extends from the collection reservoir. The vacuum tube may have an end provided with a second twist lock feature cooperating with the first twist lock feature to provide a fluid tight connection between the vacuum tube and the connector.

The above and other features, including various and novel details of construction and combinations of parts will be more particularly described with reference to the accompanying drawings. It will be understood that the details of the example embodiments are shown by way of illustration only and not as limitations of the invention. The principles and features of this invention may be employed in varied and numerous embodiments without departing from the scope of the invention.

BRIEF DESCRIPTION OF THE DRAWINGS

Non-limiting embodiments will become more fully understood from the detailed description below and the accompanying drawings, wherein like elements are represented by like reference numerals, which are given by way of illustration only and thus are not limiting of the present invention.

DESCRIPTION OF NON-LIMITING EMBODIMENTS

This disclosure is directed to a vacuum assisted drain connector ("VAD connector") that may be used to interconnect a surgical drain to a portable electronic vacuum device. Numerous and varied surgical drains are well known in this art, and the invention is not limited to any particular type of surgical drain. Also, numerous and varied portable electronic vacuum devices are well known in this art, and the invention is not limited to any particular type of portable electronic vacuum device.

Throughout this disclosure, terms relating to spatial directions (e.g., upper, top, lower, bottom, front, forward, rear, rearward, proximal, distal, etc.) are used for convenience in describing features or portions thereof, as shown in the figures. These terms do not, however, require that the vacuum assisted drain connector be maintained in any particular orientation.

Figure 1:
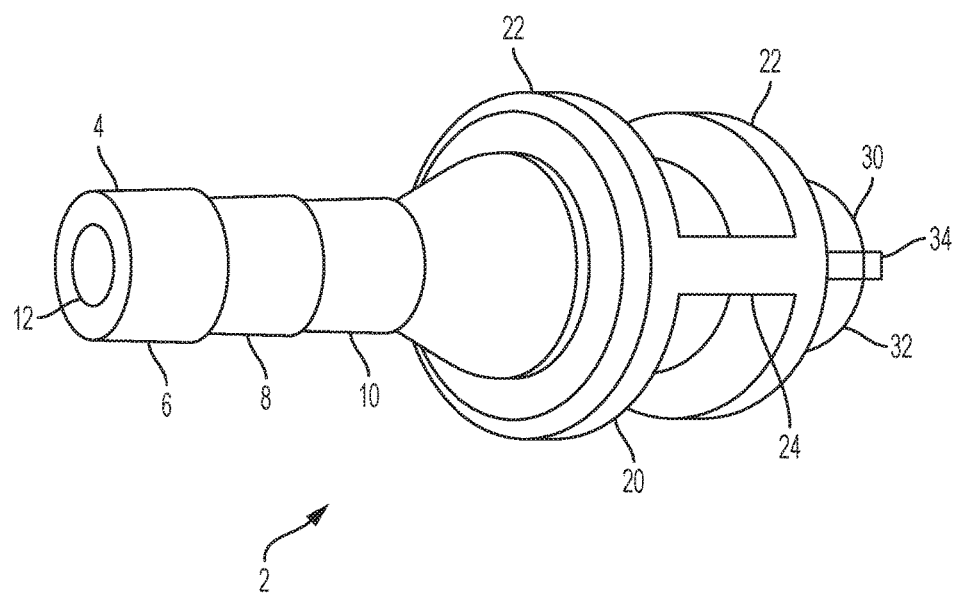
FIG. 1 is a perspective view of a vacuum assisted drain connector ("VAD connector") according to a non-limiting embodiment.

With reference to FIG. 1, the VAD connector 2 includes an elongate body. One end of the elongate body is provided with a nipple connector 4, and the other end of the elongate body is provided with the male part 30 of a twist lock connector. The nipple connector 4 includes a series of tapered surfaces 6, 8, 10. The surfaces 6, 8, 10 taper toward the free end of the nipple connector 4. The nipple connector 4 includes a circular opening 12 that leads into the interior of the elongate body.

The male part 30 of the twist lock connector is in the form of a plug 32. The plug 32 has a cylindrical shape. A pair of lugs 34 extends in a radial outward direction from the plug 32. The lugs 34 extend radially from the plug 32 in opposite directions, and therefore only one lug 34 is visible in FIG. 1.

The intermediate portion 20 of the elongate body, which is situated between the nipple connector 4 and the male part 30, includes a pair of circular flanges 22 that can be grasped to manipulate the VAD connector 2 during use. The flanges 22 may facilitate pushing and/or pulling on the VAD connector 2 in a direction parallel to a longitudinal axis 40 (see FIG. 2). One or more longitudinal ribs 24 may extend between the circular flanges 22. The ribs 24 may facilitate holding the VAD connector 2 against rotation around the longitudinal axis 40.

Figure 2:
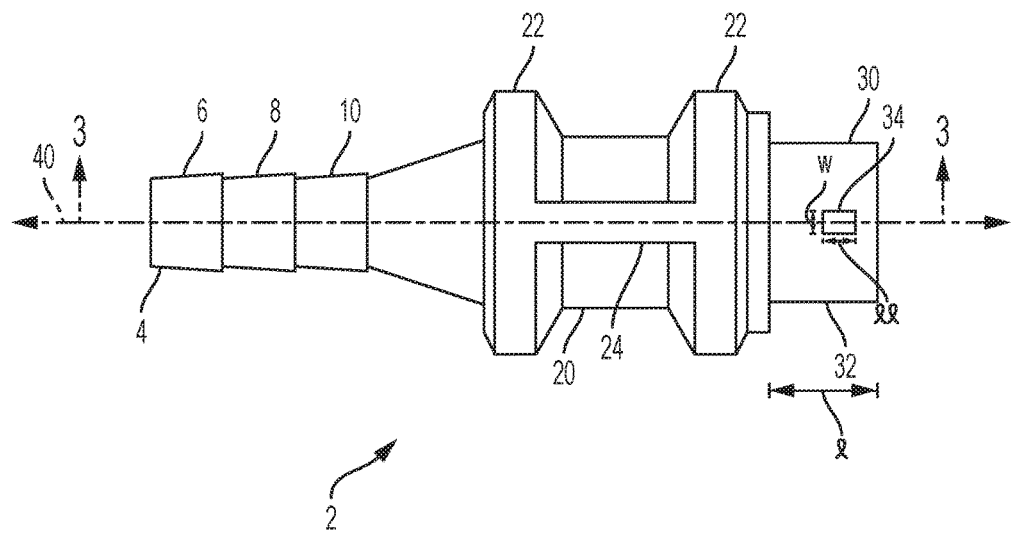
FIG. 2 is a side view of the VAD connector depicted in FIG. 1.

With reference to FIG. 2, the tapered surfaces 6, 8, 10 extend all the way around the longitudinal axis 40. The tapered surfaces 6, 8, 10 are contiguous, e.g., the largest diameter portion of one tapered surface 6 transitions to the smallest diameter portion of an adjacent tapered surface 8. In the illustrated embodiment, three tapered surfaces 6, 8, 10 are provided, but the invention is not limited in this regard.

The tapered surfaces of the nipple connector 4 may have identical dimensions. By way of example only, the smallest portion of each tapered surface 6, 8, 10 may have a diameter of 4.70 mm; the largest portion of each tapered surface 6, 8, 10 may have a diameter of 5.21 mm; and the longitudinal length of each tapered surface 6, 8, 10 may be 4.00 mm. These specific dimensions have been found to provide a fluid tight fit with numerous and varied surgical drains that are conventionally available. In alternative embodiments, the tapered surfaces 6, 8, 10 of the nipple connector 4 may have alternative dimensions.

By way of example only, the cylindrical plug 32 of the male part 30 may have a longitudinal length (l) of 6.00 mm and a diameter of 9.30 mm. The lugs 34 may have a rectangular shape as shown in FIG. 2. The longitudinal length (ll) of each lug 34 may be 1.85 mm; the width (w) of each lug 34 may be 1.38 mm; and the height (h) of each lug 34 (see FIG. 3) may be 1.56 mm. These specific dimensions have been found to provide a fluid tight fit with the "native" vacuum tube of numerous and varied portable electronic vacuum pumps. Specifically, the dimensions allow a fluid tight connection between the male part 30 of the VAD connector 2 and the female part of a twist lock connector conventionally found on the "native" vacuum tube. In alternative embodiments, the male part 30 may be provided with alternative dimensions.

Figure 3:
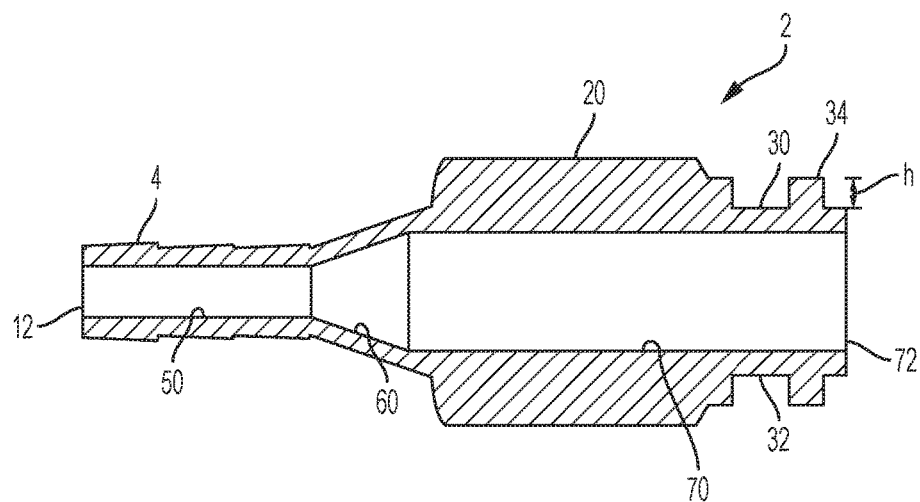
FIG. 3 is a cross-sectional view taken in the direction of line 3-3 shown in FIG. 2.

Turning to FIG. 3, the VAD connector 2 has a through passage. The though passage includes a smaller diameter cylindrical section 50 that extends from the opening 12 (or inlet opening) and through the entire length of the nipple connector 4. The smaller diameter cylindrical section 50 transitions to a frusto-conical section 60 that tapers out to a larger diameter cylindrical section 70. The larger diameter cylindrical section 70 extends through the intermediate portion 20 of the elongate body and entirely through the cylindrical plug 32. The larger diameter cylindrical section 70 terminates at a circular opening 72 (or outlet opening) provided in the male part 30. As shown, the circular opening 12 has a smaller diameter than the circular opening 72. All portions of the through passage 50, 60, 70 and the circular openings 12, 72 are centered on the longitudinal axis 40.

As discussed above, the VAD connector 2 is for use in a closed-drain system where it may be desirable to interconnect a surgical drain to a portable electronic vacuum device. Consider the example, non-limiting embodiment depicted in FIG. 4.

Figure 4:
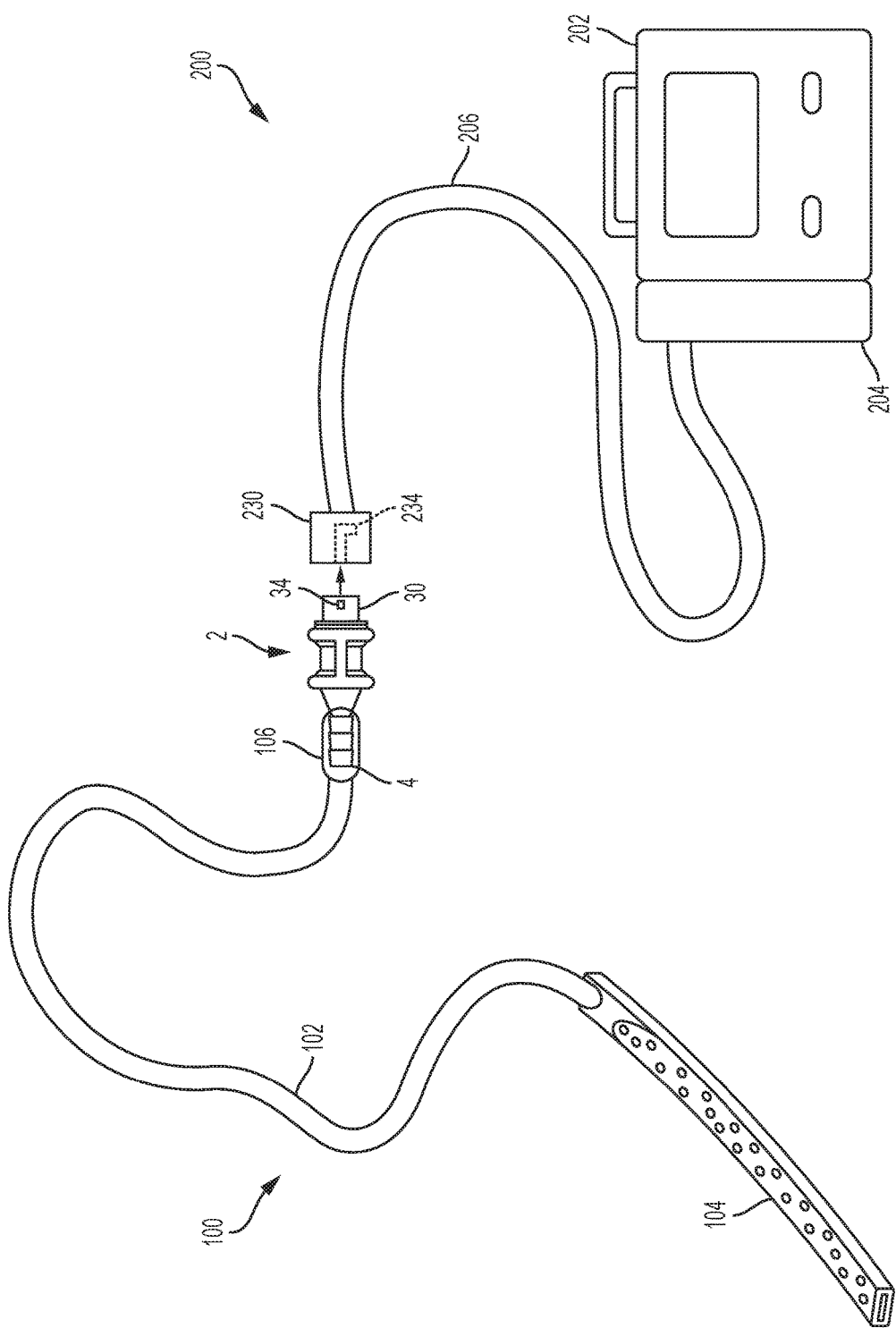
FIG. 4 is a schematic view of the VAD connector interconnecting a surgical drain to a portable electronic vacuum system.

As shown in FIG. 4, the nipple connector 4 of the VAD connector 2 may be connected to a conventional surgical drain 100, which is in the form of a flexible tube 102. The tube 102 has a distal end 104 to be implanted in a patient's body. Once the distal end 104 is implanted, the tube 102 is typically anchored to the skin by sutures. As shown, the distal end 104 has openings (or some other surface feature) for passage of fluid into the tube 102. The proximal end 106 of the tube 102 has a circular shape. The nipple connector 4 is pushed into the proximal end 106 of the tube 102. Here, the proximal end 106 of the tube 102 stretches and slides over the tapered surfaces of the nipple connector 4 to provide a fluid tight connection between the surgical drain 100 and the VAD connector 2.

It will be appreciated that numerous and varied surgical drains are well known in this art. Accordingly, the invention is not limited to the surgical drain 100 depicted in FIG. 4. It is, however, necessary that a fluid tight connection is established between the surgical drain and the VAD connector 2.

The male part 30 of the VAD connector 2 may be connected to a conventional portable electronic vacuum pump system 200. The system 200 includes a generator part 202 that creates suction or negative pressure when powered up. The generator part 202 may be battery operated and/or AC current operated. For AC current operation, the generator part 202 may be corded with a plug for connection to a wall outlet, for example. A collection reservoir 204 is coupled to the generator part 202. A native vacuum tube 206 extends from the collection reservoir 204. The free end of the vacuum tube 206 is provided with a female part 230 (or receptacle) of the twist lock connector. The female part 230 includes tracks 234 for respectively receiving the lugs 34 of the male part 30. In the illustrated embodiment, the tracks 234 (which are shown in broken lines) are provided in the form of grooves on the inside of the receptacle 230. In alternative embodiments, the tracks 234 may be provided in the form of slots that extend through the side wall of the receptacle 230.

To actuate the twist lock, the male part 30 of the VAD connector 2 may be inserted into the female part 230 of the native vacuum tube 206 as shown by the arrow in FIG. 4 (not labelled). Here, the plug 32 is aligned with the receptacle 230, such that the lugs 34 enter into the tracks 234. Upon complete insertion, the male part 30 is rotated relative to the female part 230 until the lugs 34 abut against the end of the tracks 234. In this way, the VAD connector 2 and the vacuum tube 206 may be releasably locked together in a fluid tight fashion. The parts can be unlocked and disassembled by a counter relative rotation between the male part 30 and the female part 230, followed by withdrawal of the male part 30 from the female part 230.

In the illustrated embodiment, the VAD connector 2 is provided with the male part 30 of the twist lock, while the portable electronic vacuum pump system 200 is provided with the female part 230 of the twist lock. The invention is not, however, limited in this regard. For example, the VAD connector 2 may be provided with the female part of the twist lock if the native vacuum tube is provided with the male part of the twist lock.

In the illustrated embodiment, the VAD connector 2 is of a unitary one-piece construction. The VAD connector 2 can be fabricated from numerous and varied materials that are well known in this art. By way of example only, the VAD connector can be fabricated from plastics, metals, and other materials that are well known in this art.

The use of the VAD connector 2 is straightforward. One end of the VAD connector 2 is provided with a twist lock feature to allow for a fluid tight connection to the native vacuum tube of a portable electronic vacuum pump system. The other end of the VAD connector 2 is provided with a nipple connector to allow for a fluid tight connection to a surgical drain. In this way, the VAD connector 2 can interconnect a surgical drain to a portable electronic vacuum device, which would be otherwise structurally incompatible. The vacuum pump power is turned on to create negative pressure within the vacuum tube 206, the VAD connector 2, and the surgical drain 100. Fluids from the internal, closed wound site enter into the surgical drain 100, pass through the inlet opening 12, the through passage, and the outlet opening 72 of the VAD connector 2, and pass through vacuum tubing 206 to the collection reservoir 204.

Although the foregoing description is directed to the preferred embodiments of the present teachings, it is noted that other variations and modifications will be apparent to those skilled in the art, and which may be made without departing from the spirit or scope of the present teachings.

The foregoing detailed description of the various embodiments of the present teachings has been provided for the purposes of illustration and description. It is not intended to be exhaustive or to limit the present teachings to the precise embodiments disclosed. Many modifications and variations will be apparent to practitioners skilled in this art. The embodiments were chosen and described in order to explain the principles of the present teachings and their practical application, thereby enabling others skilled in the art to understand the present teachings for various embodiments and with various modifications as are suited to the particular use contemplated. It is intended that the scope of the present teachings be defined by the following claims and their equivalents.

What is claimed is:

1. An assembly comprising:
 a connector consisting essentially of
  a nipple connector with an inlet opening,
  a first twist lock feature with an outlet opening, and
  an intermediate body portion situated between the nipple connector and the first twist lock feature;
  wherein the intermediate body portion includes a through passage that extends between the inlet and the outlet openings;
 a surgical drain having a distal end to be implanted in a patient's body, and a proximal end stretched over the nipple connector to provide a fluid tight connection between the surgical drain and the connector; and
 a portable electronic vacuum pump having a collection reservoir and a vacuum tube that extends from the collection reservoir, the vacuum tube having an end provided with a second twist lock feature cooperating with the first twist lock feature to provide a fluid tight connection between the vacuum tube and the connector;
 wherein the connector is of a unitary one-piece construction.

2. The assembly according to claim 1, wherein the nipple connector includes a plurality of circular surfaces that taper toward the inlet opening;
 wherein the circular surfaces are contiguously provided; and
 wherein the circular surfaces are of the same dimensions.

3. The assembly according to claim 1, wherein the first twist lock feature is a male part that includes
 a cylindrical plug extending from the intermediate body portion and away from the nipple connector, the plug defining at least a portion of the through passage and the outlet opening; and
 a pair of lugs extending from the plug in a radial outward direction, the pair of lugs extending radially from the plug in opposite directions.

4. The assembly according to claim 3, wherein the second twist lock feature is a female part that includes
 a receptacle; and
 tracks provided in the receptacle;
 wherein the receptacle receives the plug, such that the lugs are respectively accommodated in the tracks to releasably lock together the vacuum tube and the connector in a fluid tight fashion.

5. The assembly according to claim 1, wherein the inlet opening is smaller than the outlet opening.

6. The assembly according to claim 1, wherein the through passage includes
 a smaller diameter cylindrical section that extends from the inlet opening and entirely through the nipple connector;
 a frusto-conical section that tapers outward from the smaller diameter cylindrical section; and
 a larger diameter cylindrical section that extends from the frusto-conical section to the outlet opening.

7. The assembly according to claim 6, wherein the smaller diameter cylindrical section, the frusto-conical section, and the larger diameter cylindrical section are centered on a common longitudinal axis.

8. The assembly according to claim 1, wherein the connector includes a pair of spaced apart circular flanges situated between the nipple connector and the first twist lock feature.

9. The assembly according to claim 8, wherein the connector includes at least one rib extending between the circular flanges.

* * * * *